United States Patent [19]

Bakhos

[11] Patent Number: 5,268,054
[45] Date of Patent: Dec. 7, 1993

[54] MOUNTED MICRO-SAMPLES OF POWDERED SOLIDS AND METHOD OF PREPARING THE SAME

[76] Inventor: Youssef G. Bakhos, 1285 California Pl., Anaheim, Calif. 92805

[21] Appl. No.: 845,349

[22] Filed: Mar. 4, 1992

Related U.S. Application Data

[62] Division of Ser. No. 473,627, Jan. 31, 1990, abandoned.

[51] Int. Cl.⁵ .................................................. B32B 31/00
[52] U.S. Cl. .................................... 156/250; 156/283;
422/57; 422/58; 422/102; 435/299; 435/805;
436/810
[58] Field of Search ............... 156/250, 283; 422/56,
422/55, 57, 58, 61; 435/299, 805; 436/806, 810,
129

[56] References Cited

U.S. PATENT DOCUMENTS

| | | | |
|---|---|---|---|
| 1,866,372 | 7/1932 | Rohlfs | 156/283 |
| 2,732,324 | 1/1956 | Morris | 156/283 |
| 3,525,662 | 8/1970 | Padgett et al. | 156/283 |
| 3,682,738 | 8/1972 | Smith | 156/283 |
| 3,802,842 | 4/1974 | Lange et al. | |
| 3,881,993 | 5/1975 | Freake et al. | |
| 4,181,500 | 1/1980 | Cowsar et al. | |
| 4,234,313 | 11/1980 | Faulkner | 422/56 X |
| 4,234,316 | 11/1980 | Hevey | 422/58 X |
| 4,317,810 | 3/1982 | Halbert et al. | 422/57 X |
| 4,438,067 | 3/1984 | Siddiqi | 422/56 |
| 4,596,623 | 6/1986 | Matsumoto et al. | 156/283 |
| 4,614,554 | 9/1986 | Bate et al. | 156/283 |
| 4,649,026 | 3/1987 | Postle et al. | |
| 4,774,054 | 9/1988 | Charlton et al. | 422/57 X |
| 4,859,266 | 9/1989 | Akasaki et al. | 156/283 |
| 4,870,005 | 9/1989 | Akiyoshi et al. | 422/57 X |
| 4,886,761 | 12/1989 | Gustafson et al. | 422/58 X |
| 4,962,043 | 10/1990 | Nagase et al. | |

Primary Examiner—Patrick J. Ryan
Assistant Examiner—Merrick Dixon
Attorney, Agent, or Firm—Richard L. Gausewitz

[57] ABSTRACT

Disclosed is a mounting structure incorporating an exposed micro-sample of a particulate dry solid of interest, including a discrete adhesive covered circular plastic disc having a uniform exposed mono-layer of the particulate solid adhered to the surface of the adhesive and a handle mounted to the opposite side of the disc to facilitate exposure and retrieval of the micro-sample to and from various reactive media. The disc, adhesive and handle portion mounting the disc are of transparent generally inert, polypropylene plastic and acrylic adhesive materials, which are chemically dissimiliar to and non-reactive with the particulate solid. Also disclosed is a method for preparing essentially identical such disc mounted micro-samples from plastic sheet material having an adhesive layer thereon wherein the plastic sheet is suspended under tension, a fine powdered solid is adhered to the adhesive surface by moving an elongated tool of circular cross-section back and forth along the tensioned sheet to adhere the mono-layer, following which the excess of the powdered solid is removed and discrete circular discs of the same predetermined area are cut to produce essentially an identical particulate micro-sample of known mass at the microgram level mounted on each such discrete circular disc.

7 Claims, 4 Drawing Sheets

MOUNTED MICRO-SAMPLES OF POWDERED SOLIDS AND METHOD OF PREPARING THE SAME

This is a divisional of copending application Ser. No. 07/473,627 filed on Jan. 31, 1990 now abandoned.

This invention relates to methods for preparing uniform standardized micro-samples of dry solids and incorporating the same into mounting structures for conveniently controlled presentation to solvents and/or media chemically reactive with such solids; and, relates to the resulting mounted micro-sample structures for facilitating such presentation.

BACKGROUND OF THE INVENTION

It would be very useful to have available standardized micro-samples of various dry solids of interest in which the mass of each solid micro-sample and its exposure configuration is accurately predetermined and intact until exposed to a solvent or chemically reactive media. This would facilitate micro-techniques requiring the delivery of accurate micro-quantities of such dry solid to solvents and chemical solutions as well as facilitate investigation, both qualitatively and quantitatively of the effects of various solvents and chemically reactive media on such dry solids.

By way of illustration, there has long existed a need to facilitate the observation and/or quantification of weak chemical effects of reactive media on solids which are essentially water insoluble.

Weak chemical effects on water insoluble solids of various chemically reactive media, whether liquid, gas and/or vapor, can be difficult to meaningfully observe and accurately quantify consistently, for example, and without limitation, as in the observation or measurement of the chemical effect of weak acids such as fruit juice preparations on Hydroxy Apatite, a form of calcium phosphate which is similar in major respects to human tooth enamel.

Generally, this is due to the lack of simple procedures for accurately determining the relative minute change occuring over a short period of time in a conveniently recoverable solid sample of substantial size and mass. As a result, resort may be had to extremely long exposure and reaction times; or, stronger reactive media and/or reaction conditions (e.g., temperature) may be used to unrealistically accelerate or maximize the reaction to involve a greater proportion of the large sample, in order to be able to more conveniently observe or quantify the reaction, and then by extrapolation to estimate the reaction result over various other assumed time frames and conditions for a similiar but weaker reactive media on such solid.

In theory, orders of magnitude reduction in the initial mass of the solid sample could result in a much larger total percentage of the sample being reacted with the weak reactive media under standard conditions over conveniently brief, measured time periods so that by contrast the resulting change would be more immediately apparent and potentially more easily, accurately and realistically quantified by measurement.

Various means for holding small samples for exposure to various reactants are known. See, for example, U.S. Pat. Nos: 3,097,070; 3,220,300; 3,540,858; 3,799,742; 3,933,440; and, 4,770,856.

However, so far as is known, at the present time there is no simple procedure of general application by which multiple uniform micro-samples of dry solid, each intact and essentially of the same weight and physical configuration at the micro-gram level, are accurately and reproducibly prepared for convenient use in adding such solid to chemical solutions, or for convenient exposure to and retrieval as desired from reactive media so as to facilitate observation and accurate quantitative analysis of chemical effects of such reactive media on the solid by simple conventional techniques. At least, there is considerable need and room for improvements in this area.

Accordingly, a general object of the present invention is to provide such improvements in the form of a novel mounting structure incorporating a solid micro-sample of predetermined mass and exposure configuration intact therewith, as well as a method for accurately and reproducibly incorporating such micro-samples into such mounting structures.

SUMMARY OF THE INVENTION

In accordance with the present invention, a mounting structure incorporating an exposed micro-sample of a dry solid of interest includes a discrete, thin, disc of plastic sheet material, having front and rear sides of precisely known area. The disc preferably is circular, and is flat and uniform; and, a uniform thin layer of adhesive is adhered to and covers the front side of the disc. The disc material and adhesive are water insoluble, and chemically dissimiliar to and essentially non-reactive with the solid. The dry solid micro-sample is in the form of a fine powder having a substantially homogeneous particle size distribution covering and adhered to the surface of the adhesive layer essentially as a substantially uniform exposed mono-layer of particulate solid of accurately known mass at the micro-gram level, e.g., in terms of micrograms per $mm^2$ of area.

The discrete, circular disc may be quite small in diameter, e.g., about ⅛th inch making it suitable for in-vivo as well as in-vitro uses. The disc and the adhesive layer covering the front side thereof, both are very thin, each having a thickness at the micron level, e.g., about 30 microns. The particle size of the powdered micro-sample is very fine, e.g., less than about 45 microns.

In one embodiment of the invention, the disc material and the adhesive are transparent so as to facilitate observation of the micro-sample, and the effects of solvents and various reactive media thereon. Preferably, the adhesive is water-based acrylic and the disc material is biaxially oriented polypropylene.

Also, in one embodiment of the invention the mounting structure includes a handle mounted to the rear side of the discrete circular disc so as to facilitate exposure to and retrieval from various reactive media, as desired while minimizing need for extraneous physical contact with the disc itself. Preferably, the handle is mounted to the disc in a manner whereby the disc may be easily removed for optical examination and processing after exposure, if desired.

In another embodiment of the invention, the mounting structure includes a thin, circular cover filter having a diameter substantially in excess of that of the discrete circular disc and composed of a porous filter material chemically dissimiliar to and nonreactive with the solid. Means coupled to the rear side of the discrete, circular disc are provided for releasably mounting the circular cover filter approximately concentrically with the disc and in overlying relationship with the exposed mono-layer of particulate solid. The cover filter is useful in some applications where the reactive media may contain insoluble compounds and/or foreign materials which need to be isolated from the exposed mono-layer of particulate solid so as to allow only the diffusion of soluble material to and from the mono-layer.

In the preferred embodiment of the mounting structure of the invention, but for the mono-layer of particulate solid, all the materials of the mounting structure, including adhesives, are selected to be essentially inert with respect to a broad range of chemical compounds and solutions, so as to facilitate accurate observation and quantitative measurement of chemical effects of solvents and reactive media on the solid micro-sample without substantial interference therewith.

Materials having this property are generally well known, for example, acrylic and other polymerized synthetic resin adhesives, and various plastics including polyethylene and polypropylene, it being understood that even these materials are not resistant to all chemical compounds and solutions, e.g., certain powerful organic solvents especially under extreme conditions. The materials cited, however, are significantly chemically inert under normal conditions with respect to a broad range of chemical compounds and solutions, both organic and inorganic, and with respect to most all inorganic aqueous solutions, either acid or alkaline, and human biological fluids; hence, these materials should pose no serious interference with the qualitative or quantitative analysis of the chemical effects of most weak reactive media on micro-samples of dissimiliar solids. Of course, special materials can be selected for special applications, as required.

In accordance with the method of the present invention, essentially identical disc mounted micro-samples of a dry solid of interest are prepared by supplying a substantially flat and uniform sheet of plastic material having a substantially uniform thin layer of adhesive adhered to and covering one side thereof, such sheet material and adhesive being chemically dissimiliar to and non-reactive with the solid of interest. The sheet is supported under a predetermined uniform tension with the adhesive layer exposed. The dry solid is supplied in the form of a fine powder having a substantially uniform particle size distribution. The powdered solid is adhered to the surface of the adhesive layer to cover the same, essentially as a substantially uniform exposed mono-layer of particulate solid, while the sheet is maintained under tension. Multiple discrete discs of the same predetermined area are then cut from the resulting sheet material now intact with adhesive layer and covering of adhered mono-layer of particulate solid, so as to produce essentially an identical particulate solid micro-sample of known mass at the micro-gram level mounted on each such discrete disc. The procedure can be repeated to produce additional disc mounted micro-samples essentially identical to those first produced by using more of the same materials.

In accordance with the preferred method of the invention, the step of adhering the powdered solid to the surface of the adhesive layer is performed by first gently spreading a thick layer of powdered solid onto the adhesive layer on the tensioned sheet, then supporting an elongated slender tool member of circular cross-section to extend across the adhesive layer on the tensioned sheet, and moving said elongated tool member back and forth in a direction transverse to its length along said thick layer under gentle pressure against the exposed adhesive layer so as to adhere essentially a uniform mono-layer of exposed solid powder particles to the adhesive layer, without submerging within the adhesive beneath the mono-layer any substantial additional mass of such solid powdered particles, and, finally, removing the excess of the powdered solid. Preferably, the tool member has a cross-sectional diameter substantially in excess of, but approximately on the same order of magnitude as the maximum particle size of the powdered solid so as to facilitate this process.

BRIEF DESCRIPTION OF THE DRAWINGS

The foregoing and other important aspects of the present invention will be more fully understood by reference to the following detailed specification and examples, in conjunction with the accompanying drawings, in which.

DETAILED SPECIFICATION, WITH EXAMPLES

Figure 1:
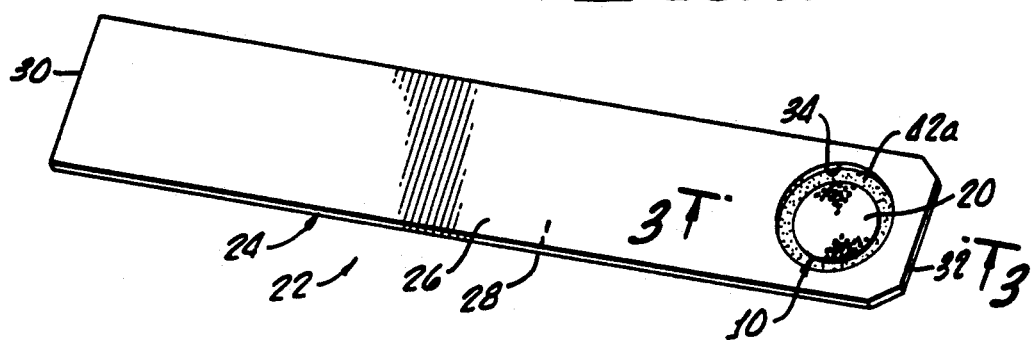
FIG. 1 is a perspective view of a preferred embodiment of the mounting structure of the invention, including the disc mounted dry solid micro-sample with elongated handle releasably mounted to the rear side of the discrete, circular disc.
Figure 2:
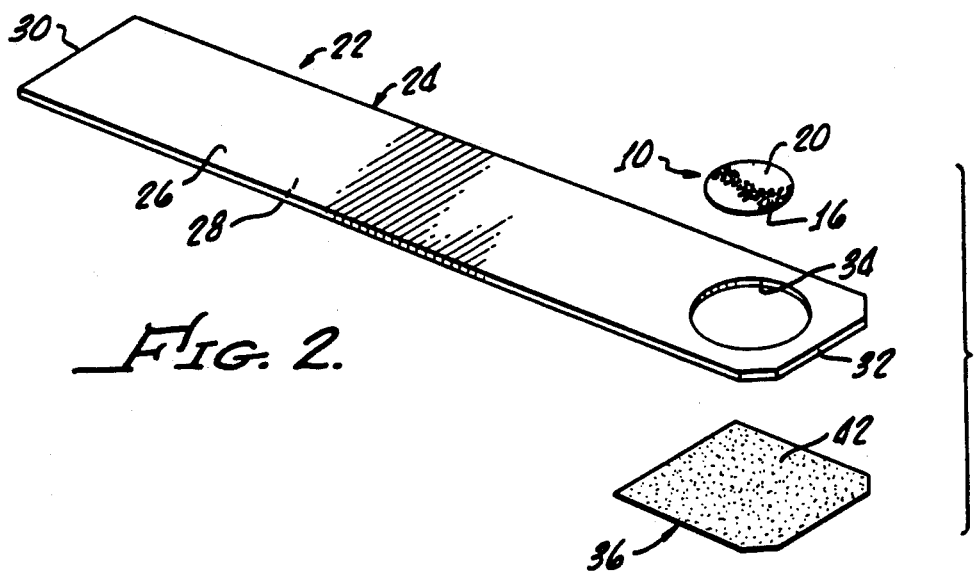
FIG. 2 is an exploded perspective view of the mounting structure of FIG. 1, illustrating its assembly.
Figure 3:
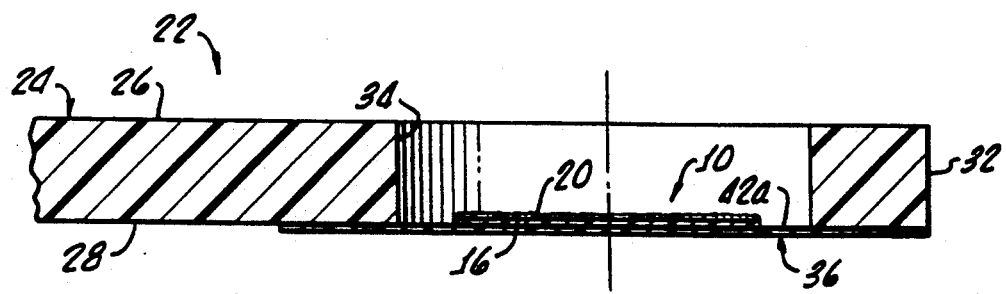
FIG. 3 is a fragmentary sectional elevation taken along line 3—3 of FIG. 1.
Figure 8:
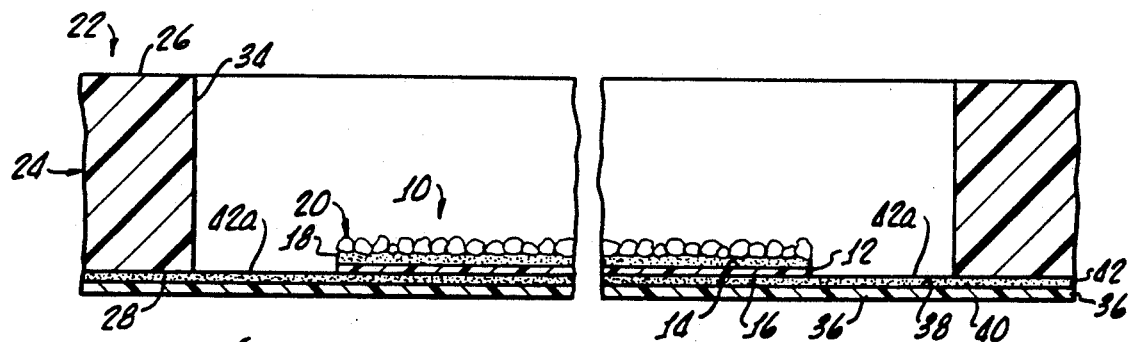
FIG. 8 is a fragmentary sectional elevation corresponding to FIG. 3, enlarged and partially cut away to illustrate the micro-structure involved, respecting the disc mounted micro-sample and its mounting to the handle.

Referring now to the drawings, as best seen in FIGS. 2 and 8, a discrete disc mounted micro-sample 10 of a dry solid of interest includes a substantially flat, uniform and discrete, thin circular disc 12 of plastic sheet material, the disc having a front side 14 and a rear side 16. A substantially uniform thin layer of adhesive 18 is adhered to and covers the front side 14 of the disc 12. The dry solid micro-sample is in the form of a fine powder having a substantially homogeneous particle size distribution and covers and is adhered to the surface of the adhesive layer 18 essentially as a substantially uniform exposed mono-layer 20 of particulate solid.

As seen in FIGS. 1-3 and 8, an elongated handle 22 is mounted to the rear side 16 of the discrete, circular disc 12. The elongated handle includes an elongated substantially flat strip 24 of plastic material having a front side 26, a rear side 28, a proximal end 30 and a distal end 32. The elongated flat strip 24 is composed of generally chemically inert polyethylene plastic material about 10 cm. long, about 1.2 cm wide and about 0.5 mm thick. By inspection it can be seen that the width and thickness of the elongated flat strip 24 substantially exceed the diameter and thickness respectively of the disc mounted micro-sample 10.

The elongated strip 24 has a circular eyelet 34 formed therein proximate the distal end 32 thereof. By inspection it can be seen that the circular eyelet 34 has a diameter substantially in excess of the diameter of the circular disc mounted micro-sample 10.

A thin uniform supporting wall 36 extends across and closes the circular eyelet 34 on the rear side 28 of the elongated strip 24. As best seen in FIG. 8, the supporting wall 36 has front and rear sides 38, 40, disposed substantially parallel to and facing respectively in the same corresponding directions as the front and rear sides 26, 28 of the elongated strip 24.

An adhesive layer 42 is disposed on and adhered to the front side 38 of the supporting wall 36 and serves as a means for adhering the rear side 16 of the discrete circular disc 12 to the front side 38 of the supporting wall 36 at a centered position within the circular eyelet 34, thus leaving an annular apron 42(a) of said adhesive layer 42 with underlying supporting wall portion, exposed between the periphery of the eyelet 34 and the periphery of the disc mounted micro-sample 10.

As illustrated, the supporting wall 36 and adhesive means 42 for adhering the discrete, circular disc 12 thereto comprise a short strip 36 of thin plastic sheet material (the supporting wall) having front and rear sides 38, 40, with the adhesive layer 42 (adhesive means) adhered to and covering the front side of the short strip 36 and adhering the short strip 36 to the rear side 28 of the elongated strip 24 of the handle 22 in areas surrounding the circular eyelet 34.

Figure 9:
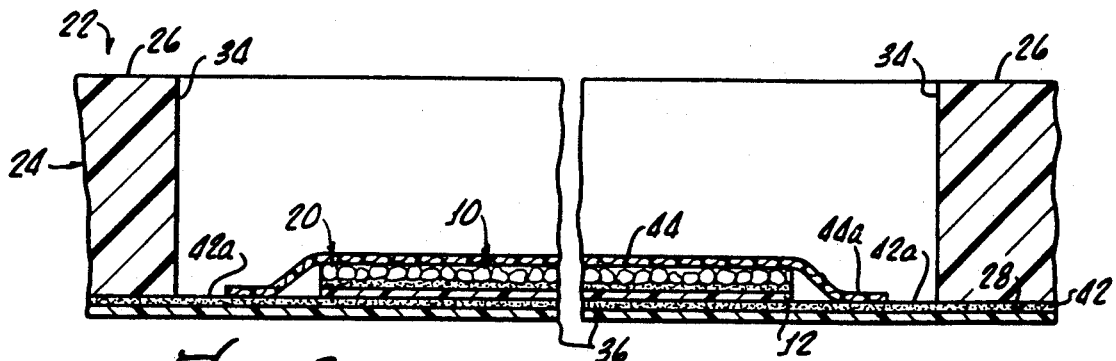
FIG. 9 is a view similar to FIG. 8, further depicting the mounting of a thin circular cover of filtering material with respect to the discrete disc in overlying relationship with the exposed mono-layer of particulate solid.

Referring now to FIG. 9, a thin circular cover 44 of filtering material extends over the exposed mono-layer 20 of particulate solid and has a diameter substantially in excess of that of the disc mounted micro-sample 10. The circular cover 44 has a thickness at the micron level of about 100 microns or less and is commercially available as a filtering material, designated as TEFLON 5.0 micron filter material from M.S.I. of 135 Slanders Road, Westborough, Mass. 01581.

As seen in Figs. 8 and 9, the supporting wall 36 and adhesive layer 42 on the front side thereof constitutes a means coupled to the rear side 16 of the discrete, circular disc 12 for mounting the circular cover 34 of filtering material approximately concentrically with the disc and in overlying relationship with the exposed mono-layer 20 of particulate solid.

The filter cover 44, as depicted in FIG. 9, has an annular marginal rim 44(a) which extends beyond the disc mounted micro-sample 10 and is adhered to the exposed adhesive layer 42 of the annular apron 42(a).

It is contemplated that the cover filter 44 would be used only under special circumstances where the reactive media to which the mono-layer is to be exposed contains insoluble compounds and/or foreign materials which are desirably isolated from the mono-layer, with the porosity of the cover filter allowing the diffusion of soluble ions to and from the mono-layer 20.

While FIG. 9 shows the cover filter 44 mounted with the disc mounted micro-sample 10 within the eyelet 44 on the handle, the same configuration can be constructed independently of its mounting on the handle, in circumstances where the handle is deemed unnecessary, in which event the supporting wall 36 and its adhesive layer 42 would be circularly die cut to the same diameter as the applied cover filter 44 directly from the adhesive covered sheet material constituting the supporting wall. The resulting structure would include the annular marginal rim 44(a) of the cover filter 44, adhered to the underlying adhesive layer of the annular apron 42(a) of the adhesive covered sheet material 36, and protruding annularly from the periphery of the disc mounted micro-sample, which could be conveniently grasped, such as with forceps (not shown).

Similarly, as seen from FIG. 8, the disc mounted micro-sample 10 can be carefully removed from the handle by cutting the apron 42(a) around the periphery of the eyelet 34 to remove the disc mounted micro-sample 10, leaving it with the protruding annular apron 42(a) which can be conveniently grasped without touching the disc mounted micro-sample 10 itself, as for example with forceps. The apron 42(a) therefor can act as a form of handle for the disc mounted micro-sample 10, and of course can be prepared separately without including the apron 42(a) as a part of a supporting wall covering an eyelet defined on the elongated strip 24, if desired.

Selection of Adhesive Covered Plastic Sheet

In investigating available plastic sheet material with adhesive layer covering one side thereof for use in fabricating the disc mounted micro-sample 10 as well as the supporting wall 36 for the disc mounted micro-sample within the circular eyelet 34, a number of commercially available clear plastic adhesive tapes were procured and tested, with attention to the following general criteria:

The tape should be free from any significant coloration, air bubbles, uneven adhesive coating layer, curling, or any noticeable faults which might cause the particulate solid to adhere unevenly or incompletely. Physical defects and irregularities were identified by visual inspection.

The tape and its adhesive layer should be free from chemical contamination in order to avoid erroneous results in qualitative and/or quantitative analysis of the effects of solvents and various reactive media on the solid micro-sample. This was determined by chemical analysis of tape samples.

The tape and its adhesive layer should be water and moisture resistant. Adhesive tapes were immmersed in water and in acid solution (0.5N HCL) for 48 hours and inspected for changes in color and adhesive properties while wet and after drying.

The tape and its adhesive should be transparent and clear to assist the user to perform visual and microscopical analysis of the solid micro-sample to be adhered thereto.

The tape should be evenly and uniformly covered with a thin adhesive layer, the thickness of the adhesive layer being at the micron level and not grossly in excess of the predominant particle size accounting for the major mass of the particulate solid. A grossly thick adhesive layer was considered undesirable in that it could interfere with the procedure of adhering the particulate solid thereto essentially as a uniform monolayer by inviting the embedding and shielding of a significant mass of solid particles in the adhesive body thus forming multi-layers of particulate solid which could cause inconsistent response to reactive media.

The adhesive tape should not be excessively elastic, whereby to cause the preparation and cutting procedures of the disc mounted micro-samples to be difficult to accurately standardize.

The tape and its adhesive layer should be chemically dissimiliar to and nonreactive to the particulate solid of interest and should be generally chemically inert to a wide range of solvents, chemical compounds and solutions, preferred materials being polyethylene or polypropylene for the tape backing sheet and a secure compatible adhesive layer of polymerized synthetic resin.

Some of the commercially available adhesive tapes failed to satisfy the moisture resistant requirement. These adhesive tapes, when immersed in water or acid solution for approximately one hour or longer, either changed color from clear to opaque or the adhesive layer peeled off partially or totally from the plastic sheet backing of the tape. Some tapes failed in other requirements.

A commercial adhesive tape found to be satisfactory for the above requirements is available under the brand name CRYSTAL CLEAR, from Moore Push Pin Co. of Wyndmoor, Pa. 109118. This tape, available on a spool, is about ¾ wide, and is catalogued as No. CCT-340-BL. The plastic sheet backing of the tape is transparent biaxially oriented polypropylene, about 0.030 mm thick, with a transparent adhesive coating or layer of the same or slightly greater thickness, the adhesive being water based acrylic.

Commercially available clear plastic adhesive tapes were investigated as a convenience for initial testing and prototype fabrication purposes. Of course, for purposes of implementing the present invention, adhesive coated plastic sheet material could be custom fabricated from specified materials, as desired.

Method Of Fabricating Mounted Micro-Samples

Figure 4:
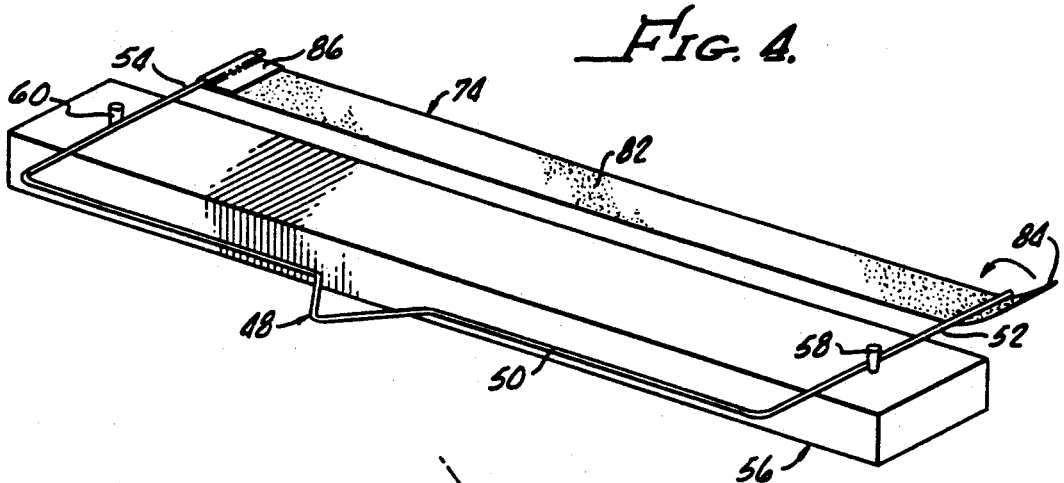
FIG. 4 is a perspective diagramatic illustration of the application of an adhesive covered plastic sheet to a tensioning tool for suspending and applying a predetermined uniform tension to the sheet.
Figure 5:
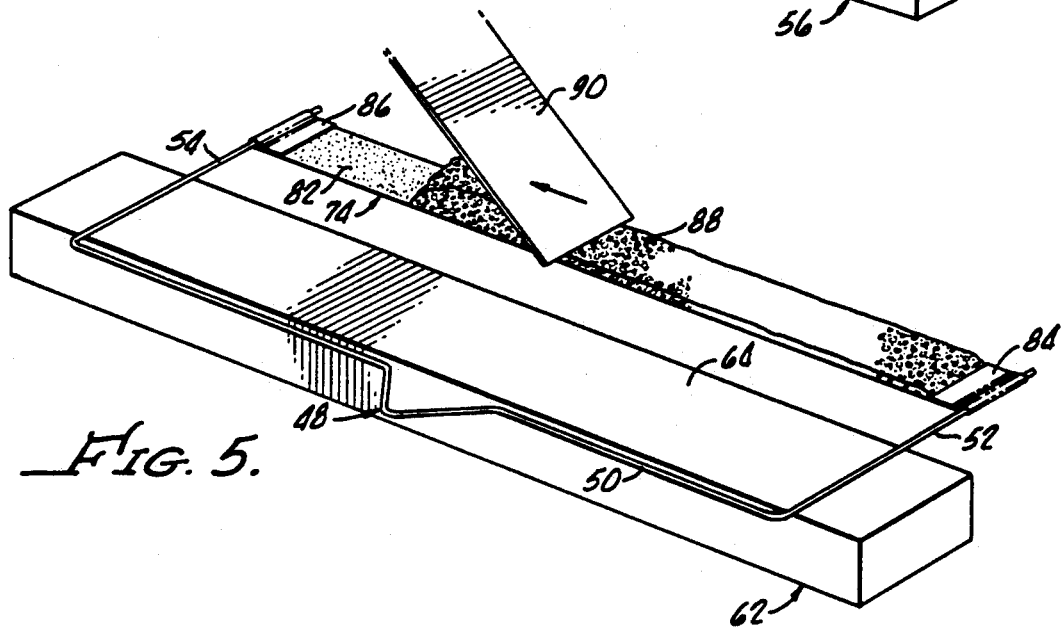
FIG. 5 is a perspective diagramatic illustration of the spreading of a thick layer of the powdered solid onto the adhesive layer on the sheet while the sheet is maintained under predetermined tension.
Figure 6:
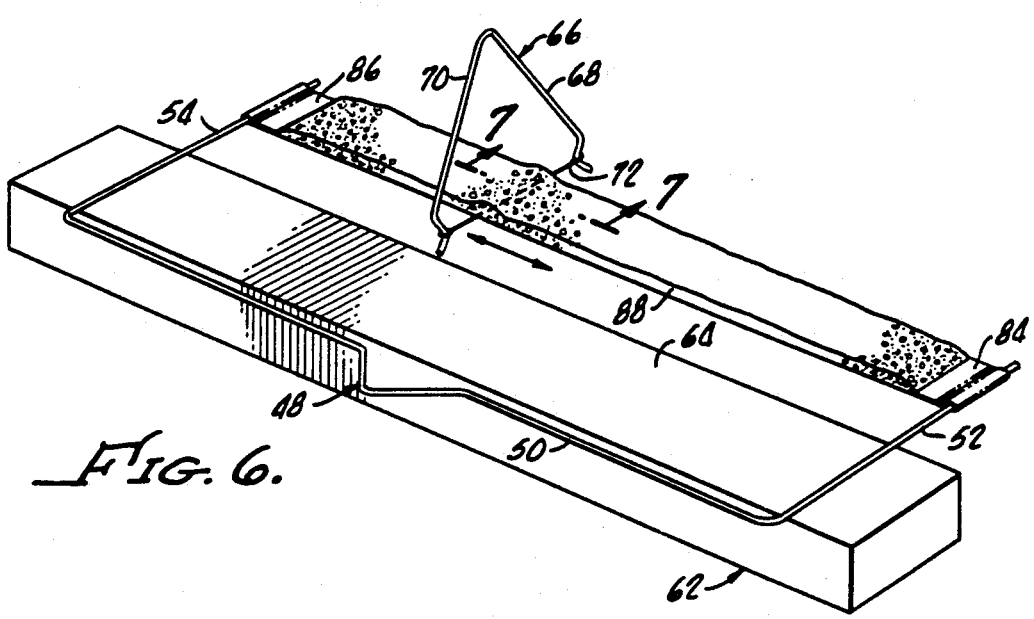
FIG. 6 is a perspective diagramatic illustration depicting the support and movement of an elongated cylindrical tool member of circular cross-section back and forth along the thick layer of powdered solid under gentle pressure against the exposed adhesive layer of the sheet while the sheet is suspended under predetermined tension so as to adhere a uniform mono-layer of solid powdered particles to the adhesive layer.

To facilitate the preparation method, certain tools were first fabricated as illustrated in FIGS. 4–7. These tools include: a tape stretcher 48 for suspending and applying a modest tension to the tape, this tension being uniform and always the same predetermined tension for successive tapes. The tape stretcher is formed of steel wire, 2 mm in diameter and about 45 cm in length, bent into the shape as shown in FIGS. 4–6, and including a base 50 and a pair of forwardly protruding coplanar legs 52, 54 giving the tape stretcher 48 an open, approximately U-shape configuration.

A stretcher holder 56 was fabricated in the form of a hard plastic plate approximately 30 cm long, 3 cm wide and 1 cm thick. Two plastic holder pins 58, 60, were centered and cemented by epoxy at a distance of 23 cm apart to the plastic plate of the holder 56.

Referring to FIG. 4, the forward protruding legs 52, 54 of the tape stretcher 48 are not normally at right angles to the base 50 of the stretcher, but are slightly divergent. As installed on the holder plate 56 between the holder pins 58, 60, the legs 52, 54 are flexed slightly inwardly toward one another in the held position. As seen in FIGS. 5 and 6, a second hard plastic plate 62 having a flat, uniform top surface 64, generally similar to the plate of the stretcher holder 56 was fabricated for use as a support base in implementing the method.

Finally, an applicator handle 66 was fabricated of steel wire, 2 mm in diameter and about 15 cm in length by bending it to the form shown in FIG. 6 with two divergent legs 68, 70 diverging generally into an open V-shape such that the distal ends of the legs were about 5 cm apart. A length of 10 lb nylon mono-filament fishing line 72 of circular cross-section was tied around the distal ends of the legs 68, 70, and tightened to close the distance between the distal ends of the legs to about 4 cm, so that the spring action of the legs 68, 70 maintained the nylon plastic filament 72 stretched.

Figure 7:
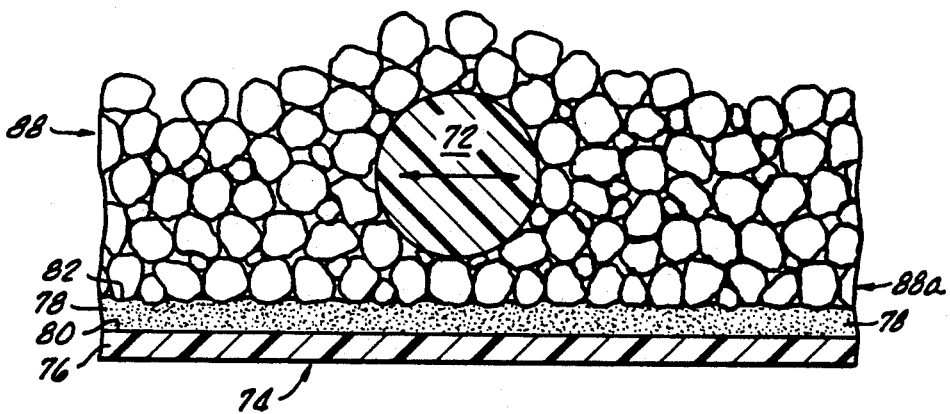
FIG. 7 is an enlarged fragmentary sectional illustration taken along line 7—7 of FIG. 6.

The circular cross-section of the nylon plastic filament 72 is illustrated in FIG. 7. The circular cross-section has a diameter about 0.180 mm. The slender nylon plastic filament 72 is thus supported by the handle 66 to serve as an elongated cylindrical applicator tool.

As illustrated in FIGS. 4–7, in fabricating the mounting structure incorporating an exposed micro-sample of a dry solid of interest, a length of about 25 cm of the CRYSTAL CLEAR adhesive tape 74 is cut and supported so as to provide a substantially flat and uniform thin sheet of plastic material 76 having a substantially uniform, thin layer of adhesive 78 adhered to and covering the top side 80 of the sheet 76, with the top surface 82 of the adhesive layer 78 being exposed.

As seen in FIG. 4, the legs 52, 54 of the tape stretcher 48 are flexed inwardly and captured between the holder pins 58, 60, following which opposite ends 84, 86 of the adhesive tape 74 are folded about the distal end portions of the stretcher legs 52, 54, and adhered to the tape, with the exposed surface 82 of the adhesive being on the top side of the tape 74.

The tape stretcher 48 is then removed from the holder 56, thus leaving the tape stretcher legs 52, 54 free to exert a divergent spring force to apply a predetermined uniform tension to the plastic sheet 76 of the tape 74.

A selected dry solid powder is sieved in a 320 mesh sieve, and shaken in order to insure homogeneous particle size distribution. The holder 48 is rested against the smooth, flat top surface 64 of the supporting base 62 with the distal end portions of the holder legs 52, 54 extending beyond the base 52 so as to freely suspend the tape 74 under uniform tension. The powdered solid is then gently spread on the exposed surface 82 of the adhesive as an even thick layer 88, about 2 mm thick, by using the straight edge of a spatula 90, as seen in FIG. 5.

As illustrated in FIGS. 6 and 7, the nylon filament 72 supported on the applicator handle 66 is inserted into the thick layer 88 of particulate solid, held horizontally to extend across the top surface 82 of the adhesive layer 78, and then moved slowly transversly of the length of the nylon filament and along the length of the tape 74 back and forth ten times while applying gentle pressure toward the adhesive surface 82.

In moving the nylon filament 72 back and forth under gentle pressure, the main bulk of the particulate solid layer 88 tends to remain on the tape 74, with the particulate solid of the thick layer flowing over the nylon filament 72 while nevertheless adhering to the adhesive 78 a substantially uniform mono-layer 88(a) of the particulate solid covering the exposed surface 82 of the adhesive.

As best illustrated in FIG. 7, the nylon filament tool 72 has a cross-sectional diameter substantially in excess of, but on the same order of magnitude as the maximum particle size of the particulate solid. The maximum particle size illustrated is about 45 microns, and the diameter of the circular cross-section of the tool 72 is about 180 microns. Preferably, the particle size range accounting for most of the mass per unit volume of the powdered solid is within about 10 to 40 microns so as to best facilitate the adherence of the exposed mono-layer 88($a$) to the adhesive surface without submerging within the adhesive beneath the mono-layer any substantial additional mass or layers of solid powder particles.

The next step is to remove the excess of solid powder particles from the tape, thus leaving only the exposed monolayer 88($a$). This is done by mechanical agitation, the impingement of an appropriate gas and/or by applying a stream of appropriate liquid, such as distilled water in the case of water insoluble solids, and then drying the tape at room temperature.

The ends of the tape are then cut from the tape stretcher 48 and multiple discrete discs of the same predetermined area are die cut from the resulting sheet material with intact adhesive layer and mono-layer of adhered solid particulate to produce essentially an identical solid micro-sample of known mass at the microgram level covering each discrete disc as illustrated by the circular disc mounted micro-sample 10 previously described with reference to FIGS. 1-3 and 8. In working with the tape both before, during and following the application of the method described above, care is taken to avoid extraneous touching or pressing against the front side thereof except only at the opposite end areas of the tape, which are later cut away and discarded.

Of course, the first time a tape is prepared with a specific particulate solid powder, the exact mass for a die cut disc mounted micro-sample of specific area must be accurately measured. Thereafter, the method can be repeated to produce additional disc mounted micro-samples of known mass essentially identical to those first produced by using more of the same materials.

Verification of Uniformity And Reproducibility

Four independent tapes with adhered monolayer were prepared using the above described method. The dry solid used to prepare these tapes was calcium carbonate powder (reagent grade), the predominant mass of which was constituted by particle sizes of about 20 to 30 microns. The adhesive covered tape used was the CRYSTAL CLEAR tape previously described. These four tape preparations are herein referred to as tape preparations (Prep.) I, II, III, and IV.

Discrete circular disc mounted micro-samples in three different diameters, hence surface areas, were die cut from the prepared tapes, as follows: Disc Size I, 7.91 mm$^2$; Disc Size II, 17.80 mm$^2$; and, Disc Size III, 31.65 mm$^2$.

First Verification

Ten mono-layer covered discs, Size II (17.80 mm$^2$) were cut from each one of the four independent tape preparations, Prep. I, II, III, and IV. The ten discrete circular discs were cut at random positions throughout each of the prepared tapes and were carefully mounted on handles using a short strip of the CRYSTAL CLEAR adhesive tape for the supporting wall to which the rear side of the discs were carefully adhered.

Calcium analysis was performed to determine the total mass of solid contained in the mono-layer on each disc, as follows: Each disc was immersed in 2.0 ml of 0.5N HCL for approximately five minutes at room temperature. Each disc was shook frequently to release the $CO_2$ bubbles formed around the exposed mono-layer on the disc. After complete dissolution of the solid, causing the adhesive covered disc to become totally clear, the acid sample was diluted to 50.0 ml with distilled water. Calcium concentration was then conventionally determined by an atomic absorption spectrophotometer (Varian Techtron, Model 1200) using the concentration mode, the results of which are set forth in Table 1 below.

TABLE 1

| DISC NUMBER | Reproducibility results of $CaCO_3$ Discs in micrograms. | | | |
|---|---|---|---|---|
| | PREP. I | PREP. II | PREP. III | PREP. IV |
| 1. | 269.7 | 267.2 | 269.7 | 272.2 |
| 2. | 269.7 | 267.2 | 269.7 | 269.7 |
| 3. | 269.7 | 264.7 | 269.7 | 269.7 |
| 4. | 269.7 | 269.7 | 267.2 | 269.7 |
| 5. | 277.2 | 269.7 | 269.7 | 269.7 |
| 6. | 269.7 | 269.7 | 269.7 | 269.7 |
| 7. | 267.2 | 269.7 | 269.7 | 267.2 |
| 8. | 272.2 | 269.7 | 267.2 | 264.7 |
| 9. | 267.2 | 269.7 | 264.7 | 267.2 |
| 10. | 269.7 | 267.2 | 264.7 | 267.2 |
| MEAN | 270.20 | 268.45 | 268.20 | 268.70 |
| STD. DEV. | 2.84 | 1.77 | 2.11 | 2.11 |

Table 1 shows the weight of calcium carbonate in micrograms for each disc calculated from the calcium analysis data. It demonstrates the reproducibility of the results. The results show that as many as 40 tests performed from the four different preparations were similar with small variations. The coefficient of variations were 0.0105, 0.0066, 0.0079, and 0.0079 for PREP. I, II, III, and IV respectively.

Second Verification $CaCO_3$ covered discs for two additional Sizes I and III were cut from tape Prep. IV and mounted to determine the reproducibility for different disc sizes. Ten discs were cut for each of the sizes I and III, and Calcium concentration was determined applying the procedure described above. The acid samples were diluted to 50.0 ml for disc Size III and diluted for 30.0 ml for disc Size I with distilled water.

TABLE 2

| DISC NUMBER | Reproducibility results of $CaCO_3$ Discs for three different disc sizes. | | |
|---|---|---|---|
| | DISC SIZE I | DISC SIZE II | DISC SIZE III |
| 1. | 121.4 | 272.2 | 472.0 |
| 2. | 118.4 | 269.7 | 454.5 |
| 3. | 118.4 | 269.7 | 472.0 |
| 4. | 118.4 | 269.7 | 479.5 |
| 5. | 121.4 | 269.7 | 467.0 |
| 6. | 121.4 | 269.7 | 472.0 |
| 7. | 116.9 | 267.2 | 469.5 |
| 8. | 116.9 | 264.7 | 462.0 |
| 9. | 119.9 | 267.2 | 464.5 |
| 10. | 116.9 | 267.2 | 472.0 |
| MEAN | 118.96 | 268.70 | 468.48 |
| STD. DEV. | 1.89 | 2.11 | 6.88 |

Table 2 shows the reproducibility data of $CaCO_3$ in micrograms for the three different disc sizes. The data shown for size II was taken from Table 1 (Prep. IV), for the purpose of comparison. The reproducibility obtained for the three disc sizes was comparable, with small variation. The coefficient of variations were 0.0159, 0.0079, and 0.0147 for the disc sizes I, II, and III respectively.

TABLE 3

Mean solid weight per $mm^2$ calculated for three different disc sizes.

| DISC SIZE | AREA $mm^2$ | MEAN TOTAL SOLID IN MICROGRAMS | SOLID PER $mm^2$ |
|---|---|---|---|
| I | 7.91 | 118.96 | 15.04 |
| II | 17.80 | 268.70 | 15.10 |
| III | 31.65 | 468.48 | 14.80 |

The calculated solid weight per $mm^2$ shown in Table 3 for the three disc sizes were similar, indicating that the particulate mono-layer on the tape preparation is uniform, and the discs can be prepared reliably in different sizes to produce accurate weights of particulate solid at the microgram level.

Figure 10:
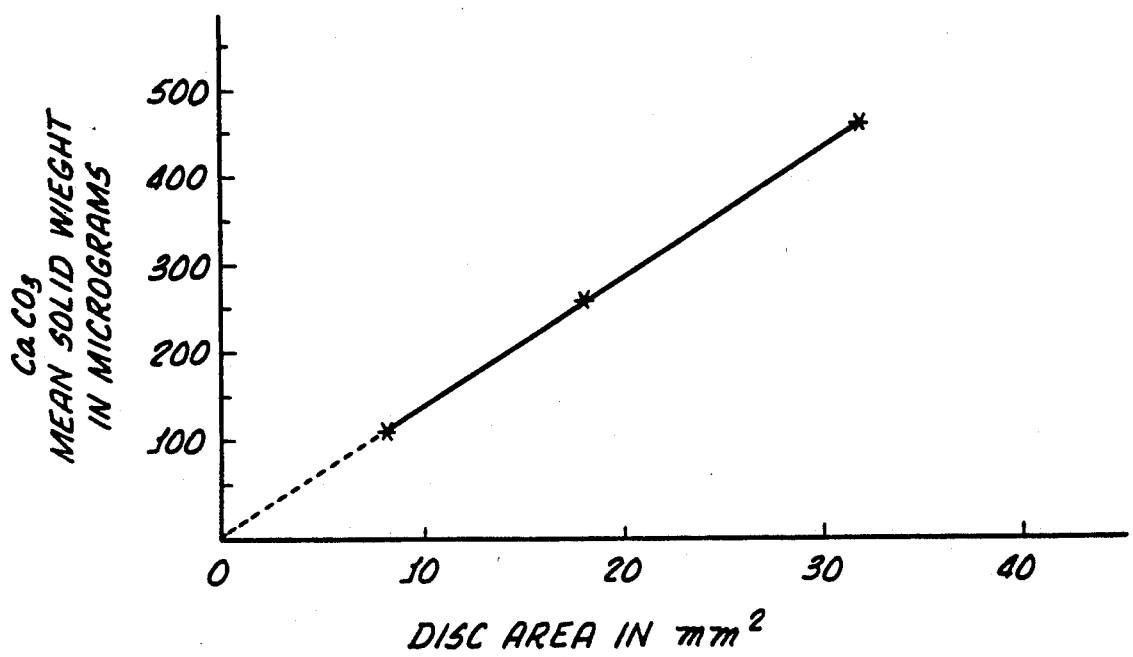
FIG. 10 is a graph depicting the relationship between disc area and mean weight of calcium carbonate as taken from examples cited in the detailed specification; and, FIG. 11 is a graph depicting the time rate of demineralization of calcium carbonate in an orange juice preparation, taken from an example cited in the detailed specification.

Referring now to FIG. 10 of the drawings, the mean value of the solid weight in micrograms is plotted against the disc area for the three disc sizes, all as taken from Table 3 above. The resulting plot in FIG. 10 is a straight line which extrapolates through the point of origin of the graph, thus indicating that the solid weight of the micro-sample is directly proportional to the disc area.

Third Verification

Anhydrous Dibasic Calcium Phosphate discs (Size II) and Iron metal powder discs (Size I) were prepared applying the same procedures described above for preparing the Calcium Carbonate ($CaCO_3$) discs.

Calcium analysis was performed to determine total solid in $CaHPO_4$ discs, size II. Each disc was immersed in 2.0 ml of 0.5N HCL for approximately five minutes while shaking at room temperature. The dissolved acid sample was then diluted to 50.0 ml with distilled water and calcium concentration was determined applying the same procedure described above for Calcium Carbonate.

Iron analysis was performed to determine total solid on the iron powder mono-layered discs, Size I. Each disc was immersed in 2.0 ml of 0.5N HCL at room temperature. After complete dissolution, 1 ml of the acid sample was diluted to 50.0 ml with distilled water and iron concentration was determined applying Atomic Absorption according to the same procedure previously described for Calcium Carbonate.

TABLE 4

Reproducibility results of Dibasic Calcium Phosphate and Iron metal Discs.

| Salt/ Metal | Number of Disc samples | Total Solid Per Disc in Milligrams Mean | St. Dev. | Solid Per $mm^2$ |
|---|---|---|---|---|
| $CaHPO_4$ | 22 | 0.1686 | 0.0055 | .0095 |
| Iron Fe | 19 | 0.6497 | 0.0129 | .0821 |

As seen in Table 4, the reproducibility data obtained for Dibasic Calcium Phosphate and iron metal were good and similar to those obtained for Calcium Carbonate.

APPLICATION EXAMPLES

The typical application procedure is to expose a specific disc mounted micro-sample for a predetermined period of time to a reactive media such as chemical solutions, vapor, water, food and beverage preparations, or human or animal biological fluids such as blood, saliva, urine, etc., and then to calculate the amount of solid micro-sample reacted, most conveniently by removing the disc mounted micro-sample from the reactive media and determining the amount of solid remaining on the disc by conventional chemical analysis and procedures where no filtration or centrifugation is required; that is, by taking advantage of the fact that the original mass of the micro-sample on the disc was accurately known at the microgram level. However, when appropriate or necessary, the reacted portion of the micro-sample can be measured directly in the reactive media. In the following examples: Example 1 illustrates the effect of a relatively large volume of orange juice preparation of micro-samples of Calcium Carbonate; and, Example 2 illustrates the effect of small microliter volumes of lemon juice preparation on micro-samples of Calcium Carbonate.

EXAMPLE NO. 1

Five discs of size II from tape Prep. IV, each mounted on a handle and incorporating a micro-sample of 268.7 micrograms of $CaCO_3$, were held by hand in fan-like configuration and immersed in 50.0 ml of fresh orange juice diluted 1:5 with tap water, for 1.0 minute with constant movement at room temperature. The discs were then removed from the diluted orange juice and washed immediately with distilled water. The excess water was removed by shaking and the discs were dried at room temperature. Calcium analysis was performed on the solid remaining on the discs after exposure, using the procedure previously described. The procedure was repeated for juice exposure times of 3.0 and 6.0 minutes, with the following results:

TABLE 5

Effect of orange juice on Calcium Carbonate Disc, Size II, (17.80 mm)

| Exposed Time in Minutes | Remaining Solid In Micrograms (measured) Mean | St. Dev. | Dissolved Solid In Micrograms (Calc.) |
|---|---|---|---|
| 1.0 | 236.240 | 5.749 | 32.460 |
| 3.0 | 185.297 | 4.803 | 83.403 |
| 6.0 | 91.899 | 11.084 | 176.801 |

The data of Table 5 shows a near linear relationship in the amount of dissolved $CaCO_3$ solid with exposure time. The coefficient of variations of the remaining Calcium Carbonate were 0.0243, 0.0259, and 0.1206 for the exposure time 1.0, 3.0, and 6.0 minutes respectively. The amount of Calcium Carbonate dissolved in 3.0 minutes was more than two fold larger than the 1.0 minute exposure and the 6.0 minutes exposure was larger by more than five fold.

Figure 11:
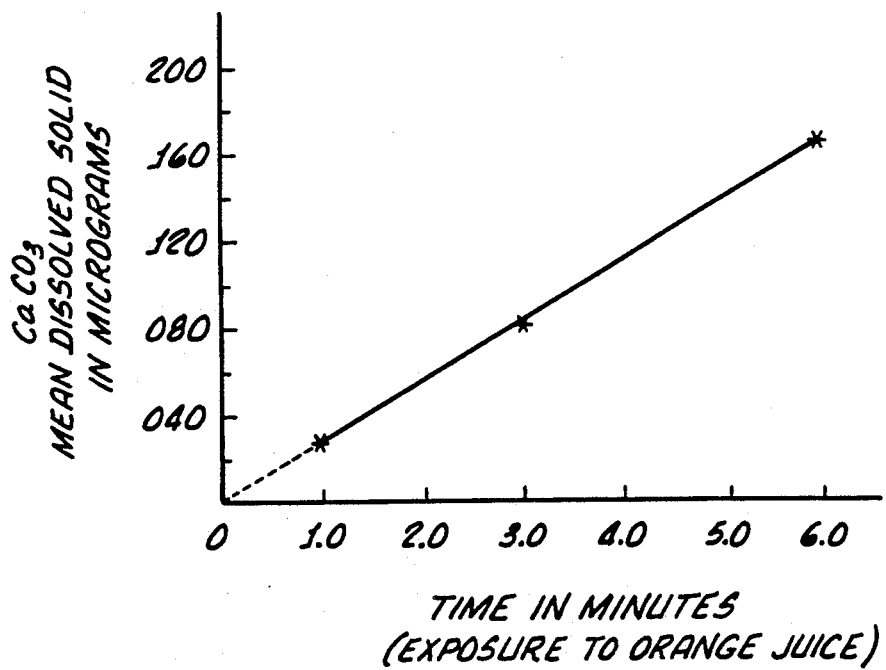

Referring to FIG. 11 of the drawings, the functional relation between the amount of dissolved $CaCO_3$ solid and the exposure time to the orange juice preparation is shown by a straight line extrapolated through the origin by plotting the results of Table 5.

EXAMPLE NO. 2

Five $CaCO_3$ discs from tape preparation IV (size I) each having a solid micro-sample of 118.96 micrograms were disposed horizontally, and 20 microliters of fresh lemon juice diluted 1:1 with distilled water was applied on each disc with constant stirring at room temperature. After exactly 1.0 minutes, the discs were immediately washed with distilled water. The excess water was removed by shaking and the discs were dried at room temperature. Calcium analysis was performed using the same procedure previously described The total procedure was repeated for juice exposure times of 2.0 and 3.0 minutes. The results were as follows:

TABLE 6

Effect of Microliter-sample of lemon juice on Calcium Carbonate Discs, Size I, (7.91 mm)

| Exposed Time in Minutes | Remaining Solid In Micro-grams (Measured) | St. Dev. | Dissolved Solid In Micrograms (Calc.) |
|---|---|---|---|
| 1.0 | 86.904 | 2.119 | 32.066 |
| 2.0 | 51.843 | 3.761 | 67.127 |
| 3.0 | 27.969 | 3.532 | 91.001 |

The data in Table 6 shows significant difference in the amount of solid dissolved for each exposure time. The coefficient of variations of the remaining Calcium Carbonate were 0 0244, 0.0725, and 0.1263 for the exposure time 1.0, 2.0, and 3.0 minutes respectively. Two and three fold increase in the amount of solid dissolved was noticed after 2.0 and 3.0 minutes exposure respectively. The amount of dissolved solid was very nearly directly proportional to the exposure time to the lemon juice as similarly observed for the orange juice in Example No. 1. The results indicate that a reactive media volume of 20 microliters was sufficient to cause significant and proportional change in the amount of solid dissolved from the disc in relatively short periods of time.

As the Calcium Carbonate dissolves and the adhesive layer on the disc becomes exposed to the reactive media, and the adhesive covered disc clears, no foreign fibers from the lemon or the orange juice was noticed to be adhered to the tape. As expected, the tape adhesive loses its adhering property while wet.

DISCUSSION

The uniform mono-layer adhered to the adhesive surface allows the user to visually detect even minor changes in the micro-sample. The changes are either due to solid dissolution as in the case of the $CaCO_3$ discs, or to changes in the chemical constituents of the micro-sample. An example of the latter is the red coloration taken on by an iron powder covered disc after exposure to a humid atmosphere for several hours, due to the $Fe_2O_3$ formed on the exposed surface of the iron particles in the mono-layer on the disc. Such visual inspections may be performed by looking at the disc to view reflected or transmitted light, with or without the aid of magnification. The use of transparent materials for the disc and adhesive layer facilitates observation and optical analysis.

The elongated handle 22 for the disc 10, as illustrated in the drawings, is very useful for in-vitro techniques. Any number of these structures can be conveniently stored together in a sealed container from which the individual structures may be conveniently removed by hand by grasping the proximal ends 30 thereof. The mono-layer 20 on each disc is protected from abrasion by adjacent structures by virtue of its disposition near the bottom of the relatively deep circular eyelet 34; and, the use of transparent tape and adhesive layer for the supporting wall 36 which closes the bottom of the eyelet, such as the CRYSTAL CLEAR tape used to fabricate the adhesive covered disc, facilitates optical inspection and analysis without requiring removal of the disc mounted micro-sample 10 from the handle.

Of course, the handles greatly facilitate the insertion and retrieval of a disc mounted micro-sample into solvents and reactive media, either individually or several simultaneously. Different forms of handles can be coupled to the rear side 16 of the disc, including very small handles to facilitate in-vivo micro-techniques.

Because the plastic disc is very thin, it has a certain degree of flexibility which can be of assistance in in-vivo uses. For example, discs covered with a mono-layer of powdered hydroxy apatite can be applied to a human tooth covered with plaque inter-orally after a sugar rinse to study cariogenicity of sugar in various solutions and food stuffs.

In the following claims, the unqualified term "disc" is used in a general sense to denote a discrete, thin piece or chip, which may be circular or of other geometric configuration, such as rectangular, polygonal, elliptical or crescent shaped.

I claim:

1. A method for producing essentially identical mounted micro-samples of a dry solid of interest, said method comprising the steps of:
   (a) supplying a substantially flat and uniform thin sheet of plastic material, said plastic sheet having a substantially uniform thin layer of adhesive adhered to and covering one side thereof, said sheet material and adhesive being chemically dissimilar to and essentially non-reactive with said solid;
   (b) supporting said sheet under a predetermined uniform tension with said adhesive layer exposed;
   (c) supplying said solid in the form of a dry fine powder having a substantially uniform particle size distribution;
   (d) adhering said solid powder to the surface of said adhesive layer to cover said surface essentially as a substantially uniform exposed mono-layer of solid powder particles; and,
   (e) cutting multiple discrete discs of the same predetermined area from the resulting sheet material with adhesive layer and mono-layer of adhered solid particles, to produce essentially an identical particulate solid micro-sample of known mass at the micro-gram level mounted on each such discrete disc, whereby the method can be repeated to produce additional disc mounted micro-samples essentially identical to those first produced, by using more of the same materials.

2. The method of claim 1, wherein the step of adhering said solid powder to the surface of said adhesive layer essentially as a substantially uniform exposed mono-layer of solid powder particles, comprises the steps of:
   (a) gently spreading a thick layer of the powdered solid onto the adhesive layer on the sheet;
   (b) supporting an elongated slender too member of circular cross-section to extend across the adhesive layer on said sheet;
   (c) moving said elongated tool member back and forth in a direction transverse to its length along said thick layer under gentle pressure against said exposed adhesive layer so as to adhere essentially a uniform mono-layer of at least partially exposed solid powder particles to said adhesive layer, without submerging within said adhesive beneath said mono-layer any substantial additional layers of such solid powdered particles; and, (d) removing the excess of said powdered solid.

3. The method of claim 1, wherein said discrete discs are circular.

4. The method of claim 2, wherein said tool member has a cross-sectional diameter substantially in excess of, but on the same order of magnitude as, the maximum particle size of said powdered solid.

5. The method of claim 2, wherein said plastic sheet and layer of adhesive adhered thereto each have a thickness of about 30 microns, and wherein the particle size of said solid powder is less than about 45 microns and less.

6. The method of claim 5, wherein said plastic sheet is transparent biaxially oriented polypropylene, and said adhesive is transparent water-based acrylic.

7. The method of claim 5, wherein the predominate mass of said solid powder comprises particle sizes between about 10 and 40 microns.

* * * * *